United States Patent [19]

Miller et al.

[11] Patent Number: 4,540,405
[45] Date of Patent: Sep. 10, 1985

[54] DISPOSABLE SYRINGE SLEEVE

[75] Inventors: Gabriel M. Miller; Timothy B. Cowen, both of Barboursville; Philip R. Palin, Huntington, all of W. Va.

[73] Assignee: Cilco, Inc., Huntington, W. Va.

[21] Appl. No.: 512,921

[22] Filed: Jul. 12, 1983

[51] Int. Cl.³ .............................................. A61M 5/26
[52] U.S. Cl. .................................... 604/232; 604/241
[58] Field of Search .............. 604/187, 232, 197, 241; 128/1.1

[56] References Cited

U.S. PATENT DOCUMENTS

| | | | |
|---|---|---|---|
| 3,076,455 | 2/1963 | McConnaughey et al. | 604/232 |
| 3,583,399 | 6/1971 | Ritsky | 604/232 |
| 3,895,633 | 7/1975 | Bartner et al. | 604/232 |
| 4,112,945 | 9/1978 | Helixon et al. | 604/232 |
| 4,122,836 | 10/1978 | Burnett | 128/1.1 |

Primary Examiner—John D. Yasko
Attorney, Agent, or Firm—Lyon & Lyon

[57] ABSTRACT

A disposable plastic syringe sleeve (2) is disclosed. The syringe sleeve (2) is adapted to receive the body (42) of a conventional glass hypodermic syringe (40), which glass hypodermic syringe (40) has a luer tip (44) extending therefrom. A threaded section (10) formed at one end (12) of the syringe sleeve (2) cooperates with the luer tip (44) of the glass hypodermic syringe (40) and the threads (54) on a hypodermic needle (52) to provide positive luer locking for the needle 52. An enlarged finger grip (20) with a retaining mechanism (32) is formed at the other end (24) of the syringe sleeve (2). The retaining mechanism (32) operates to retain the glass hypodermic syringe (40) in position after the syringe sleeve (2) has received the syringe body (42).

9 Claims, 4 Drawing Figures

DISPOSABLE SYRINGE SLEEVE

TECHNICAL FIELD

The present invention is directed to an apparatus for use with a hypodermic syringe and more particularly concerns a disposable sleeve structure which fits over the body of a glass hypodermic syringe to provide increased finger grip area for medical personnel using the syringe and to provide positive luer locking for the hypodermic needle attached to the syringe.

BACKGROUND ART

Syringe assemblies comprising plastic syringe holders or barrels adapted to receive and support glass cartridges containing medicaments have heretofore been developed for use in the medical field. U.S. Pat. No. 3,811,411 issued to Sarnoff, U.S. Pat. No. 3,884,229 issued to Raines, et al., and U.S. Pat. No. 3,895,633 issued to Bartner, et al. are all directed to syringe assemblies of the type just described. In all three patents, the glass cartridges are inserted into the syringe holders and engaged by retaining means. A stoppered open end in each glass cartridge is designed to engage an inner needle projecting into the interior of the syringe holder. The inner needle may simply be formed from the inner end of the cannula needle itself, as in the aforementioned Sarnoff patent, or it may be formed as part of an intermediate "transfer"-type needle structure as in the Raines, et al. and Bartner, et al. patents.

Prior art syringe holders such as those discussed above serve a beneficial purpose by combining the advantages of storing medicaments in chemically inert glass cartridges with the advantages of using inexpensive, disposable plastic syringes to administer the medicament to patients. Unfortunately, these advantages are not fully exploited, inasmuch as the prior art glass cartridges must be specially manufactured to fit the syringe holders, and attendant increases in the cost of the syringe assemblies offsets somewhat the savings realized by constructing the syringe holders out of plastic. For this reason, many chemically-active medicaments are still packaged in conventional glass syringes, i.e., glass syringes having hypodermic needles or cannulas affixed thereto. The prior art does not, however provide plastic syringe holders designed to fit over conventional glass syringes.

It is thus an object of the present invention to provide a plastic syringe holder into which a conventional glass syringe may be inserted.

It is a further object of the present invention to provide a syringe holder in the form of a plastic sleeve structure adapted to fit over a glass hypodermic syringe, wherein the plastic sleeve structure is constructed with large flanges for the purpose of increasing the finger grip area otherwise associated with conventional glass syringes.

It is still a further object of the present invention to provide a plastic sleeve structure capable of fitting over a glass hypodermic syringe having a luer tip wherein a threaded section at one end of the sleeve structure furnishes positive locking for the hypodermic needle mounted onto the luer tip of the glass syringe.

It is another object of the present invention to provide a plastic syringe holder having integrally formed snap-style tabs for retaining a glass hypodermic syringe therein.

These and other objects of the present invention are accomplished by a disposable plastic syringe sleeve adapted to receive a conventional, luer-tipped glass syringe. Snap-style tabs on the plastic sleeve grip the flange of the glass syringe, thereby retaining the glass syringe inside the plastic sleeve. A threaded section on the plastic sleeve functions in combination with the luer tip of the syringe to provide positive locking for the syringe hypodermic needle. In addition, an enlarged flange area is formed on the plastic sleeve adjacent the snap-style tabs to provide a relatively large finger grip for the person administering medicine from the glass syringe.

BRIEF DESCRIPTION OF THE DRAWINGS

The various objects, features and advantages of the present invention will become more apparent upon consideration of the following Brief Description of the Drawings in conjunction with the Best Mode for Carrying Out the Invention, wherein.

BEST MODE FOR CARRYING OUT THE INVENTION

Figure 1A:
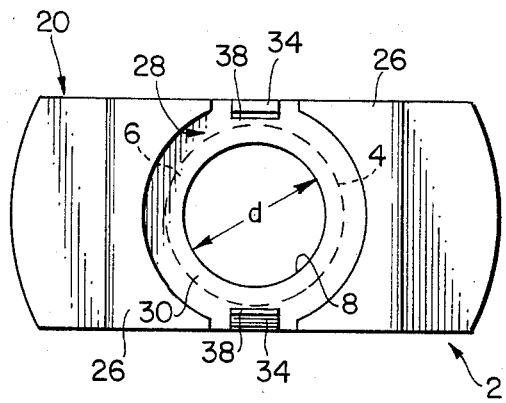
FIGS. 1A–1C respectively provide top, front, and right elevation views of a syringe sleeve constructed in accordance with the present invention.
Figure 1B:
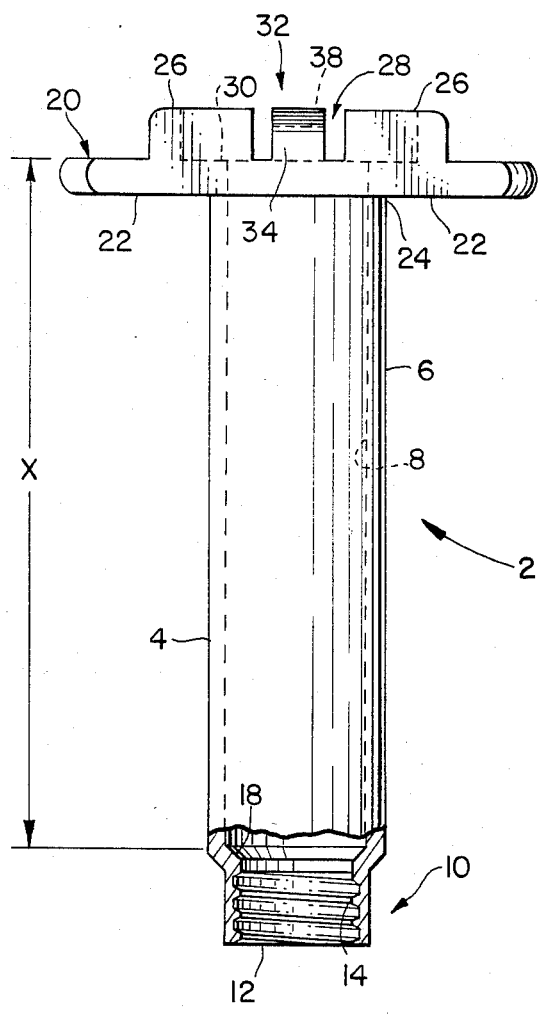
Figure 1C:
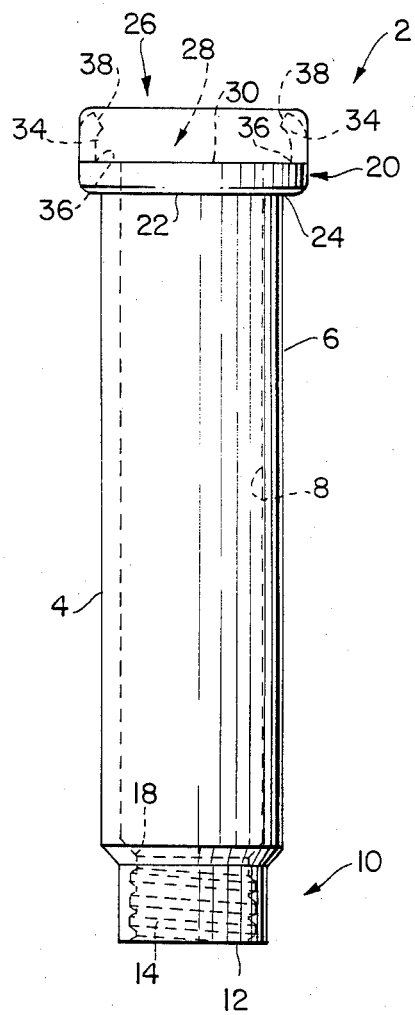

The present invention basically comprises a disposable sleeve-like structure adapted for receiving and positively retaining a glass hypodermic syringe of the type conventionally employed by medical personnel for subcutaneous administration of liquid medicaments. As illustrated in FIGS. 1A–1C, syringe sleeve 2 includes a hollow sleeve member 4 having a relatively thin sidewall 6 arranged in generally cylindrical configuration. This cylindrical configuration conforms to the cylindrical cross-section normally associated with hypodermic syringes, although other configurations could be utilized if necessary to accommodate hypodermic syringes having non-standard shapes. The inner diameter d of hollow sleeve member 4 may be suitably adjusted to provide a close fit between the inner surface 8 of sidewall 6 and the body (not shown in FIGS. 1A–1C) of the hypodermic syringe.

A threaded section 10 formed at one end 12 of hollow sleeve member 4 contains internal threads 14, as can be seen to best advantage in the cut-away portion of FIG. 1B. Internal threads 14 are designed to cooperate with the luer threads of a locking luer needle (not shown in FIGS. 1A–1C), thus providing a "luer lock" system for postively securing the needle to the hypodermic syringe during use. This latter feature is more fully described in connection with FIG. 2. The inner surface of sidewall 6 flares somewhat at the beginning of threaded section 10, establishing a circumferential transition surface 18. Circumferential transition surface 18 accommodates the change in inner diameter d which occurs between inner surface 8 and internal threads 14 and may serve as a stop for the body (not shown in FIGS. 1A–1C) of the hypodermic syringe, as will also be described in greater detail in connection with FIG. 2.

A finger grip 20 having a grip area 22 is formed at the end 24 of hollow sleeve member 4 opposite threaded section 10. Finger grip 20 may be curved to follow the contours of the fingers. A raised portion 26 on finger grip 20 is hollowed out to furnish a cavity 28 for receiving the flange (not shown in FIGS. 1A–1C) which surrounding the open end of the hypodermic syringe. The syringe sleeve 2 is dimensioned such that the distance X from the base 30 of cavity 28 to the transition surface 18 separating threaded section 10 from the remainder of the hollow sleeve member 4 approximates the distance between the flange of the syringe body and the front end of the syringe body. A syringe retaining mechanism 32 consisting of a pair of snap-style tabs 34 projects upward from the base 30 of cavity 28. Referring specifically to FIG. 1C, tabs 34 arc slightly inward to create pockets 36 at the juncture of the tabs and base 30 of cavity 28. The tips of the tabs are cut at an angle to provide camming surfaces 38. When so arranged, the tabs 34 act to positively engage the flange, and hence the hypodermic syringe, as the hypodermic syringe is inserted into hollow sleeve member 4.

If desired, syringe sleeve 2 can be fabricated from a clear plastic material such as Lexan 144 using injection mold techniques. In this manner, all of the structural features of the syringe sleeve can be formed as an integral unit, with attendant reduction in manufacturing costs making possible the sale of the syringe sleeve as a low-cost disposable item. Injection molding techniques additionally contribute to the provision of a practical finger grip 20. That is, owing to the pecularity of glass-working techniques, the area of the flange which can be obtained by drawing out the sides of a glass syringe body is somewhat limited. In contrast, the plastic material from which syringe sleeve 2 is fabricated can be easily worked to provide a relatively large grip area 22, thus facilitating the ease with which medical personnel administering medicament from the glass syringe can grip the syringe sleeve. As a net result, greater stability during use of the glass syringe is achieved with a consequent reduction in trauma to the patient receiving the injection of medicament from the syringe.

Figure 2:
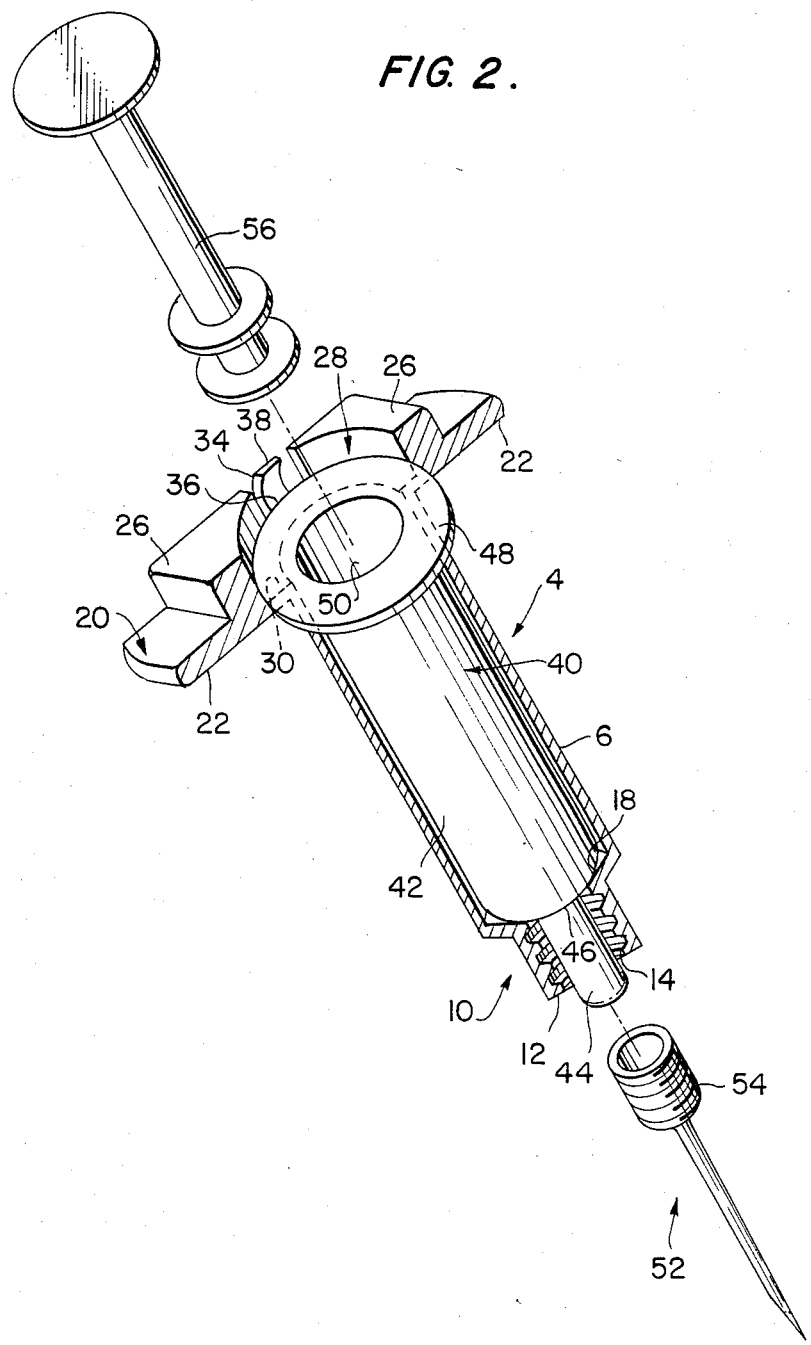
FIG. 2 is a cut-away perspective view of a syringe sleeve into which a conventional glass syringe has been inserted.

Turning to FIG. 2, a glass hypodermic syringe 40 can be seen fully inserted into syringe sleeve 2. Hypodermic syringe 40 includes a syringe body 42 with a luer tip 44 extending from the end wall 46 thereof and a glass flange 48 circumferentially extending about the open end 50 of the syringe body 42. Preferably, hypodermic syringe 40 is a standard or conventional glass syringe. When fully inserted in syringe sleeve 2, flange 48 slides over the camming surfaces 38 of snap-style tabs 34. Tabs 34 flex slightly outward to permit passage of the flange 48, whereupon the flange "snaps" into the pockets 36 formed at the juncture of the tabs 34 and the base 30 of cavity 28. The tabs thereafter return to their inward arcing position to retain hypodermic syringe 40 inside syringe sleeve 2. Removal of the hypodermic syringe 40 from syringe sleeve 2 can be accomplished by simply pushing the syringe backwards past the snap-style tabs 34 until the tabs release flange 48, permitting the hypodermic syringe to be withdrawn from the syringe sleeve.

As previously discussed, the inner diameter d of hollow sleeve member 4 approximates the outer diameter of syringe body 42 to prevent gross movement of the syringe body relative to the hollow sleeve member. When the glass flange 48 of the hypodermic syringe 40 is resting in the pockets 36 below snap-style tabs 34 on the finger grip 20 of syringe sleeve 2, end wall 46 of the syringe body 42 abuts transition surface 18 while the luer tip 44 extending from end wall 46 passes through the threaded section 10 of hollow sleeve member 4. The distance X between the base 30 of cavity 28 in finger grip 20 and transition surface 18 is ideally equal to the length of the syringe body 44 of hypodermic syringe 40, although in practice some gap between end wall 46 and transition surface 18 is permissible. A hypodermic needle 52 having luer-locking threads 54 machined at one end thereof is then positioned over the luer tip 44 of the hypodermic syringe 40 and tightened into threaded section 10. Cooperation between the internal threads 14 of the threaded section and the luer-locking threads on the hypodermic needle 52, in combination with the grip exerted by the luer tip 44 of the hypodermic syringe, establish a positive or luer-locking system which is effective in securing the hypodermic needle 52 to the hypodermic syringe against back-pressure which may build up inside syringe body 42 during medicament injection. A plunger mechanism 56 is finally inserted in the open end 50 of syringe body 44 to complete assembly of the hypodermic syringe.

The present invention has been described in the form of one preferred embodiment. It is nevertheless understood that various modifications to the structure of the syringe sleeve disclosed herein may be made by those skilled in the art without departing from the scope or spirit of the present invention, and it is the inventors' intent to be bound only by the limitations of the following claims.

What is claimed is:

1. An apparatus for use with a hypodermic syringe having a syringe body with a tip extending directly therefrom and a hypodermic needle shaped to fit over the tip, the hypodermic needle having external threads formed thereon, said apparatus comprising a sleeve means for receiving the hypodermic syringe, said sleeve means including a hollow sleeve member into which the syringe body is inserted, saod hollow sleeve member having a cross-sectional shape adapted to fit the cross-sectional shape of the syringe body, said hollow sleeve member also having a hollow threaded section disposed at one end thereof, said hollow threaded section being formed with a cross-section through which the top of the hypodermic syringe passes as the syringe body is inserted into said hollow sleeve member such that said hollow threaded section surrounds the tip of the hypodermic syringe after said sleeve means has received the hypodermic syringe, said hollow threaded section further being formed with internal threads which engage the external threads on the hypodermic needle when the hypodermic needle is mounted on the tip extending from the syringe body.

2. An apparatus as set forth in claim 1, wherein said hollow sleeve member includes a sidewall arranged in a cylindrical configuration, said sidewall having an inner diameter which approximates the outer diameter of the syringe body.

3. An apparatus as set forth in claim 2, wherein said inner diameter of said sidewall changes at said hollow threaded section to form a transition surface which separates said hollow threaded section from the remainder of said hollow sleeve member.

4. An apparatus as set forth in claim 1, wherein the syringe body of the hypodermic syringe has a flange circumferentially disposed about one end thereof and said sleeve means is fabricated from plastic such that said hollow sleeve member has a finger grip formed thereon with a grip area larger than the area presented by the flange of the hypodermic syringe.

5. An apparatus as set forth in claim 4, wherein said finger grip includes a retaining means for securing the hypodermic syringe to said sleeve means when the hypodermic syringe is inserted into said hollow sleeve member.

6. An apparatus as set forth in claim 5, wherein said retaining means includes at least two flexible tab means which expand to grip the flange on the hypodermic syringe when the hypodermic syringe is inserted into said hollow sleeve member.

7. An apparatus as set forth in claim 6, wherein said flexible tab means include at least two tab members projecting in arcuate fashion from said finger grip such that pockets are formed at the juncture of said tab members and said finger grip, said pockets receiving the flange of the hypodermic syringe when the hypodermic syringe is inserted into said hollow sleeve member.

8. An apparatus as set forth in claim 6, wherein said finger grip further includes a raised portion having a cavity formed therein to receive the flange on the hypodermic syringe, said cavity having a base surface on which said tab means are formed.

9. An apparatus comprising a glass hypodermic syringe having a syringe body with a tip extending from one end thereof and a flange circumferentially disposed about the other end thereof, said glass hypodermic syringe also having a hypodermic needle shaped to fit over said tip extending from said syringe body, said hypodermic needle having external threads formed thereon, said apparatus also comprising a disposable plastic sleeve means for receiving said glass hypodermic syringe, said sleeve means including a hollow sleeve member into which said glass hypodermic syringe is inserted, said hollow sleeve member having a finger grip formed thereon with a grip area larger than the area presented by said flange of said glass hypodermic syringe, said hollow sleeve member further having a threaded section disposed at one end thereof which surrounds said tip of said hypodermic syringe when said syringe body is inserted into said hollow sleeve member, said threaded section bveing formed with internal threads which engage said external threads on said hypodermic needle when said hypodermic needle is mounted on said tip extending from said syringe body.

* * * * *